United States Patent
Calas et al.

[11] Patent Number: 5,873,719
[45] Date of Patent: Feb. 23, 1999

[54] DENTAL REAMER

[75] Inventors: Paul Calas, Toulouse; Jean-Marie Vulcain, Vitre; Jean-Marie Badoz, Doubs; Hubert Euvrard, Geneuille, all of France

[73] Assignee: Micro-Mega International Manufactures, Besancon, France

[21] Appl. No.: 840,800

[22] Filed: Apr. 16, 1997

[30] Foreign Application Priority Data

Apr. 17, 1996 [FR] France ................................ 9604987

[51] Int. Cl.⁶ .................................................. A61C 5/02
[52] U.S. Cl. .......................................... 433/102; 433/165
[58] Field of Search ............................ 433/81, 102, 165, 433/224

[56] References Cited

U.S. PATENT DOCUMENTS

| 4,538,989 | 9/1985 | Apairo, Jr. et al. | 433/102 |
| 4,634,378 | 1/1987 | Leonard | 433/102 |
| 4,836,780 | 6/1989 | Buchanan | 433/102 |
| 5,213,499 | 5/1993 | Levy | 433/102 |
| 5,429,504 | 7/1995 | Peltier et al. | 433/165 |

*Primary Examiner*—Nicholas D. Lucchesi
*Attorney, Agent, or Firm*—Weiser and Associates, P.C.

[57] ABSTRACT

A dental reamer having one or more cutting sections and one or more spiral grooves. The dental reamer has at least one cutting edge having a cutting point, characterized in that a tangent to the cutting point tends to superimpose itself on a tangent to a diameter of a circle in which the cutting sections are inscribed, wherein the diameter passes through the cutting point. The invention provides a reaming cut that, in a surprising manner, reduces or even eliminates the spiral displacement (i.e., uncontrolled advancement of the reamer) that results from rotation of the prior-art reamers, while still maintaining an excellent reaming efficacy.

14 Claims, 1 Drawing Sheet

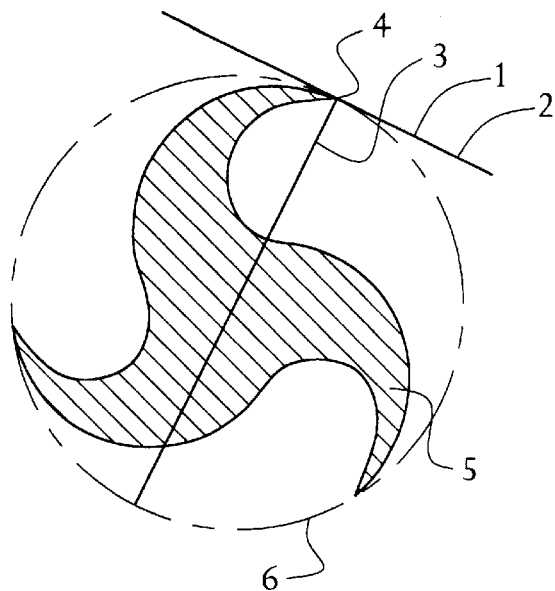
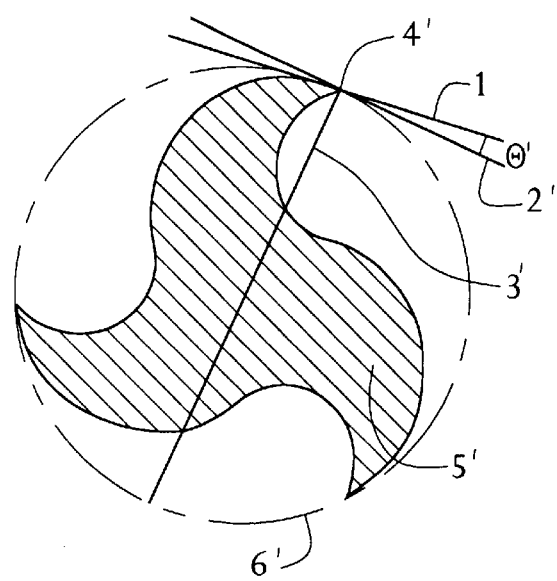
FIG. 1a
FIG. 1b
(Prior Art)
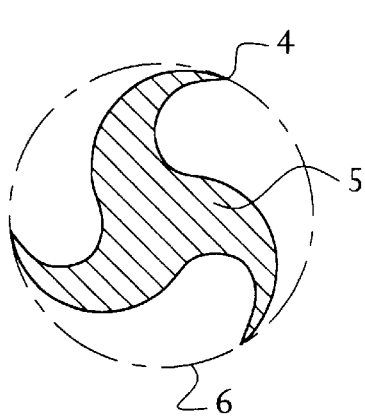
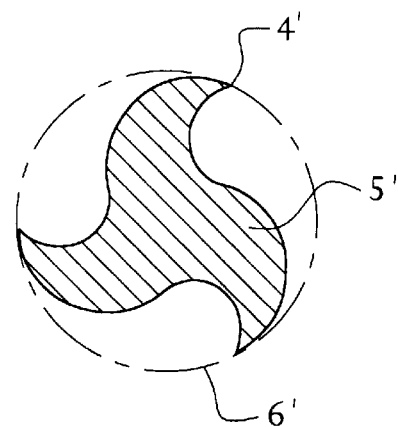
FIG. 2a
FIG. 2b
(Prior Art)

— DENTAL REAMER —

DENTAL REAMER

BACKGROUND OF THE INVENTION

1. Field of the Invention

The present invention relates to dentistry equipment, and, in particular, to dental reamers.

2. Description of the Related Art

Dental reamers having one, two, or three spiral grooves have already been described. For example, French patent application 82 20903 describes a dental reamer that tapers down to its tip, of the type having three spiral grooves with a progressive pitch such that the free spaces between the cutting edges increase as one moves from the tip of the reamer towards its handle.

Although French patent application 82 20903 provides an improvement over dental reamers having only one or two spiral grooves, the improvement is limited. In practice, the dental reamer proposed in French patent application 82 20903 has been found to result in undesirable spiral displacement in the canal to be reamed during the continuous rotation of root canal treatment. As used in this specification, spiral displacement refers to the tendency of reamers of the prior art to advance within the canal as a result of the rotation of the reamer itself, rather than solely as a result of pressure applied by the dentist. If spiral displacement occurs, the dentist will not have complete control over the reaming process which can lead to serious problems for the patient.

The present invention addresses this limitation in the prior art. Further aspects and advantages of this invention will become apparent from the detailed description which follows.

SUMMARY OF THE INVENTION

The present invention is directed to a dental reamer having one or more cutting sections and one or more spiral grooves, exhibiting at least one cutting edge having a cutting point, characterized in that a tangent to the cutting point tends to superimpose itself on a tangent to a diameter of a circle in which the cutting sections are inscribed, wherein the diameter passes through the cutting point. In preferred embodiments, the cutting sections are designed to eliminate spiral displacement during continuous rotation of the reamer within a canal.

BRIEF DESCRIPTION OF THE DRAWINGS

Other aspects, features, and advantages of the present invention will become more fully apparent from the following detailed description, the appended claims, and the accompanying drawings in which:

FIGS. 1a and 2a are cross-sectional views of a reamer, according to one embodiment of the present invention; and FIGS. 1b and 2b are cross-sectional views of a prior-art reamer.

DETAILED DESCRIPTION

The present invention proposes to resolve drawbacks in the prior art by addressing the effects of continuous rotation observed in the use of the prior-art reamers, where continuous rotation is believed to be the source of undesirable spiral displacement. In accordance with embodiments of the present invention, a reduction in spiral displacement is achieved with a dental reamer that tapers down to its tip, of the type having one or more spiral grooves exhibiting at least one cutting edge for the reaming of the root canals of teeth, characterized in that the tangent to each cutting point of the reamer tends to superimpose itself on the tangent to the diameter of the circle in which the cutting sections of the reamer are inscribed, where the diameter passes through the cutting point. In a preferred embodiment, the tangent to each cutting point is merged with the tangent to the corresponding diameter.

According to certain embodiments of the present invention, the dental reamer has one or more spiral grooves having a progressive pitch, in a manner such that the free spaces between the cutting edges increase as one moves from the tip towards the handle of the reamer.

FIG. 1a shows a cross-sectional view of a reamer, according to one embodiment of the present invention. FIG. 2a shows a cross-sectional view of the reamer of FIG. 1a, at a location closer to the tip of the reamer. The reamer of FIGS. 1a and 2a has three spiral grooves, each having a corresponding cutting edge. For each cutting edge, the tangent (1) to the cutting point (4) tends to superimpose itself on the tangent (2) to the diameter (3) of the circle (6) in which the cutting sections (5) are inscribed, where the diameter (3) passes through the cutting point (4). In a preferred embodiment, the tangent (1) to the cutting point (4) and the tangent (2) to the diameter (3) are merged (i.e., co-linear).

As in prior-art reamers, reamers of the present invention have a handle and a shaft terminating in a tip. In preferred embodiments, the reamer tapers down to its tip and each of the spiral grooves has a progressive pitch such that the free spaces between cutting edges increase as one travels from the tip of the reamer to its handle. Although the reamer of FIGS. 1a and 2a has three spiral grooves, it will be understood that the present invention applies more generally to reamers having one or more spiral grooves.

FIGS. 1b and 2b show cross-sectional views of a prior-art reamer. In the prior-art reamer, the tangent (1') to the cutting point (4') of each cutting edge forms an angle (θ') with the tangent (2') to the diameter (3') of the circle (6') in which the cutting sections (5') of the reamer are inscribed, where the diameter (3') passes through the cutting point (4').

As shown in FIGS. 1a and 2a, in accordance with the present application, the angle between the tangent (1) to the cutting point (4) and the tangent (2) to the diameter (3) of the circle (6) tends toward zero. FIGS. 1a and 2a illustrate the preferred embodiment in which the two tangents (1, 2) are merged (i.e., θ=0°).

The present invention provides a reaming cut that, in a surprising manner, reduces or even eliminates the spiral displacement (i.e., uncontrolled advancement of the reamer) that results from rotation of the prior-art reamers, while still maintaining an excellent reaming efficacy. This gives the dentist considerably more control over the drilling, and it is noteworthy that with this new reamer, the dentist can gently apply a forward pressure to controllably advance the reamer, as opposed to the prior art where the dentist would have to "hold back" the forward self-propelled motion of the reamer.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A dental reamer comprising one or more cutting sections, one or more spiral grooves, and at least one cutting edge defined by inner and outer surfaces and having a cutting point, wherein a tangent to the outer surface at the cutting point tends to superimpose itself on a tangent to a diameter of a circle in which the cutting sections are inscribed, wherein the diameter passes through the cutting point.

2. The reamer of claim 1, wherein the tangent to the outer surface at the cutting point is merged with the tangent to the diameter.

3. The reamer of claim 1, comprising three spiral grooves.

4. The reamer of claim 1, wherein the reamer tapers down to its tip.

5. The reamer of claim 4, wherein the tangent to the outer surface at the cutting point is merged with the tangent to the diameter.

6. The reamer of claim 4, comprising two or more cutting edges wherein at least one spiral groove has a progressive pitch such that free space between cutting edges increases away from the tip of the reamer.

7. The reamer of claim 6, wherein the tangent to the outer surface at the cutting point is merged with the tangent to the diameter.

8. The reamer of claim 7, comprising three spiral grooves.

9. The reamer of claim 1, wherein spiral displacement due to rotation of the reamer is reduced.

10. A dental reamer comprising one or more cutting sections and one or more spiral grooves, wherein the cutting sections are designed to eliminate spiral displacement during continuous rotation of the reamer within a canal and the dental reamer comprises at least one cutting edge defined by inner and outer surfaces and having a cutting point, wherein a tangent to the outer surface at the cutting point tends to superimpose itself on a tangent to a diameter of a circle in which the cutting sections are inscribed, wherein the diameter passes through the cutting point.

11. The reamer of claim 10, wherein the tangent to the outer surface at the cutting point is merged with the tangent to the diameter.

12. The reamer of claim 10, comprising three spiral grooves.

13. The reamer of claim 10, wherein the reamer tapers down to its tip.

14. The reamer of claim 10, comprising two or more cutting edges, wherein at least one spiral groove of the one or more spiral grooves has a progressive pitch such that free space between cutting edges increases away from the tip of the reamer.

* * * * *